United States Patent
Wood et al.

(10) Patent No.: US 6,536,263 B1
(45) Date of Patent: Mar. 25, 2003

(54) GAUGES FOR TESTING SAND IN OR FOR GOLF COURSE SAND BUNKERS

(75) Inventors: Donald C. Wood, Temecula, CA (US); Todd D. Harman, Long Beach, CA (US)

(73) Assignee: Roger Cleveland Golf Company, Inc., Cypress, CA (US)

( * ) Notice: Subject to any disclaimer, the term of this patent is extended or adjusted under 35 U.S.C. 154(b) by 0 days.

(21) Appl. No.: 09/603,434

(22) Filed: Jun. 23, 2000

Related U.S. Application Data

(60) Provisional application No. 60/141,312, filed on Jun. 25, 1999.

(51) Int. Cl.[7] .............................. G01N 3/42; G01N 3/48; G01N 3/00; B23Q 17/00
(52) U.S. Cl. ....................... 73/82; 73/78; 73/81; 73/84; 73/85
(58) Field of Search ................................ 73/81, 84, 85, 73/82, 78

(56) References Cited

U.S. PATENT DOCUMENTS 4,887,459 A * 12/1989 Thomas ......................... 73/81

* cited by examiner

*Primary Examiner*—Daniel S. Larkin
*Assistant Examiner*—Katina Wilson
(74) *Attorney, Agent, or Firm*—Parkhurst & Wendel, L.L.P.

(57) ABSTRACT

A sand penetrability gauge for golf course bunker sand, having a probe shaft for penetrating into bulk sand, a weight or spring for reproducibly applying force to advance the probe shaft into bulk sand, the probe shaft being movably connected to the weight or spring, and measuring indicia associated with the probe shaft for measuring displacement of the probe shaft, with a cross-sectional area of the probe shaft and the force of the weight or spring selected so that the measuring indicia will provide a displacement measurement when the probe is driven into golf course sand bunker sand.

5 Claims, 2 Drawing Sheets

FIG. 1
FIG. 2
FIG. 4
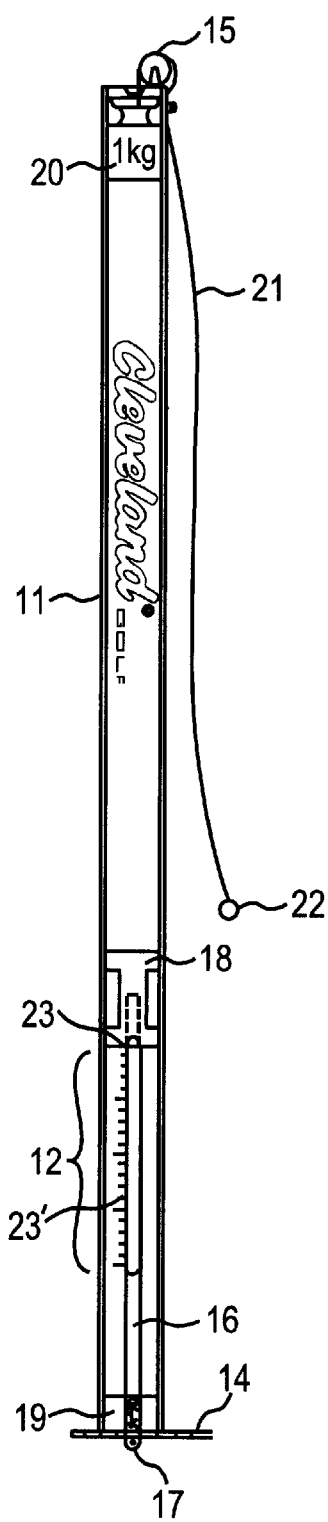
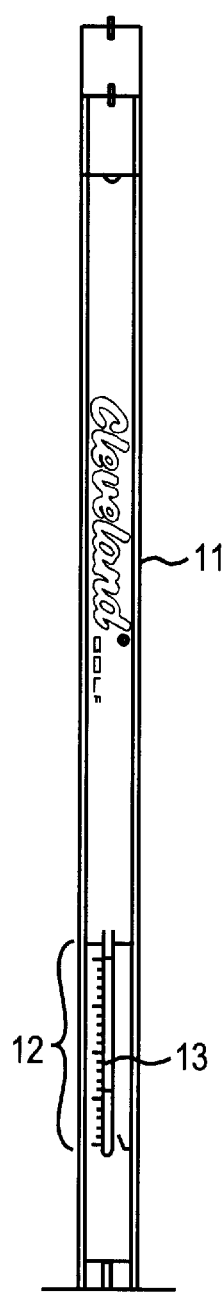
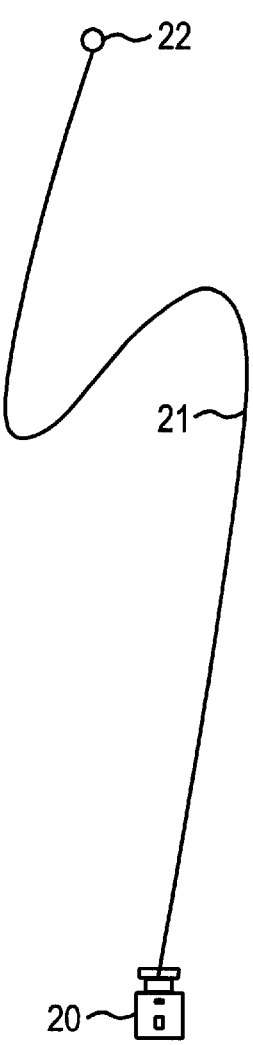
FIG. 3
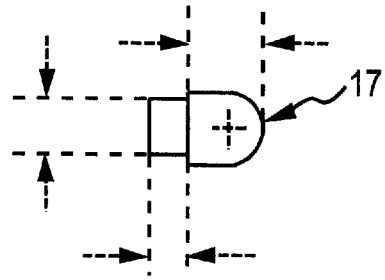

GAUGES FOR TESTING SAND IN OR FOR GOLF COURSE SAND BUNKERS

CROSS-REFERENCE TO RELATED APPLICATIONS

This application claims the benefit of the Jun. 25, 1999 filing date of U.S. Provisional Patent Application Serial No. 60/141,312.

FIELD OF THE INVENTION

This invention relates to novel apparatus and gauges for testing characteristics of sand in or for golf course sand bunkers.

BACKGROUND OF THE INVENTION

Each hole on a golf course comprises not only a teeing ground from which play is commenced and a green including the pin and hole which is the ultimate target, but usually also includes a fairway. Additionally, adjacent the fairway there is usually a region of rough, less improved terrain, and various hazards may exist in either the fairway or rough. The rough and such hazards are typically to be avoided by the golf player to maximize the opportunity of minimizing the number of strokes required to play a golf hole from tee to green.

The United States Golf Association, hereinafter USGA, Rules of Golf, 1998–1999, Rules 12 and 13, define a hazard as any bunker or water hazard. Those rules also specifically define "bunker" as "a hazard consisting of a prepared area of ground, often a hollow, from which turf or soil has been removed and replaced with sand or the like." A bunker wherein turf or soil has been replaced with sand is typically called a sand bunker or sand trap. When a player's ball lands in a sand bunker, USGA Rule 13-4 specifies that before making a stroke to attempt to play the ball from the hazard, the player is prohibited from (a) testing the condition of the hazard or any similar hazard, (b) touching the ground in the hazard with a club or otherwise, and (c) touching or moving a loose impediment lying in or touching the hazard. Thus, in seeking to play a ball with his club from a sand bunker, a golfer must play the ball as it lies, without testing or touching the sand before playing the ball.

A sand trap is unique among golf course hazards in that sand traps are typically highly maintained. Sand traps typically undergo a daily mechanical grooming or raking as a regular part of golf course maintenance, and divots and footprints are eliminated by raking after use by a player. Despite these attempts to maintain similar-conditions in a trap for every player, the condition of the sand at any specific location in any sand bunker, and particularly conditions from one bunker to another, even on the same course, may vary. And, there are no particular rules governing the nature of the sand or like material which may be present in a sand bunker. Thus, the characteristics of the sand in a sand bunker, and the condition of the sand at the particular location where a player's ball comes to rest in a sand bunker, may vary greatly, making play from sand bunkers unpredictable.

The specific characteristics of sand in a sand bunker may include sand grain size, grain shape and the distribution of different grain sizes and shapes in a representative sample of sand in any bunker. Furthermore, the granular density and bulk density of the sand in a representative sample from any sand bunker may vary. Still further, other conditions such as the depth of the sand, its wetness or moisture content, and its compactness, that is hardness versus fluffiness, are further factors which may contribute to the unpredictability of play of a golf shot from a sand bunker.

While, in the past, some tests for sand consistency have been conducted in laboratories away from a particular sand bunker and the particular sand in any particular sand bunker, such tests have been for the purpose of attempting to assess the potential for an inbound golf ball to either bury itself or produce an inaccessible, so-called fried-egg, lie in such sand. There are no generally accepted objective methods for standardized field testing of sand in sand bunkers on golf courses.

However, experienced golfers will make equipment choices, such as selection of a sand wedge having a certain sole width and thus bounce properties, and certain choices concerning where to place the ball in the player's stance, how open or closed to have the face of the sand wedge at impact with the ball, and how to swing the sand wedge, based upon the player's understanding of the characteristics of the sand at or near the location where the player's ball rests in a sand bunker. More accurate knowledge concerning the characteristics of the sand upon which the player's ball lies would assist experienced sand players during practice sessions in more accurately making an appropriate club selection and in determining stance/ball location, club face position and swing strength in executing a sand shot from a particular lie in a particular sand trap. Thus, an objective method for standardized field testing of sand in golf course sand bunkers will be of great assistance to golfers in learning to execute sand shots.

BRIEF SUMMARY OF THE INVENTION

Thus, it is an object of the present invention to overcome the above-discussed problems and needs unsatisfied by the prior art.

It is a further object of the present invention to provide a sand gauge capable of measuring the relative softness or bulk density of sand at a given location in a golf course sand trap.

Another object of the present invention is to provide a device for measuring the resistance of the sand to a device being pressed into the sand of a golf course sand trap.

Still another object of the present invention is to provide a device for assisting a player in evaluating golf course sand trap sand conditions, for correlating practice shot techniques and the results thereof from such sand conditions.

Other objects and further features of the present invention are described hereafter in this specification.

In a first embodiment, an advantageous sand gauge of the present invention is constructed for measuring the relative softness or bulk density of sand in a golf course sand trap, wherein the device includes a tube with a blunted spike at the bottom thereof and a substantial weight in the top of the tube for release and fall down the tube, impacting the spike and driving the spike into the sand. The depth to which the spike is driven into the sand is a measure of the softness or bulk density of the sand.

In another embodiment, an advantageous sand gauge of the present invention comprises an outer housing wherein a combination probe shaft and gauge is mounted, and a spring is mounted for compression between the housing and the probe shaft to regulate load on the probe shaft. The device is used by pushing its lower probe end into the sand bunker sand being tested, and stop pushing the device toward the sand when the bottom of the outer housing contacts the sand, recording the probe displacement at that moment.

BRIEF DESCRIPTION OF THE DRAWINGS

The aforementioned embodiments and further features of the advantageous system of the present invention are illustrated and further explained in conjunction with the following drawings, wherein:

FIG. 1 is a partially cut-away side view of an upright gravity drop spike sand gauge of the present invention;

FIG. 2 is a view of the exterior tube portion of a gravity drop spike sand gauge like that of FIG. 1;

FIG. 3 is a side view of the sand spike tip insert of the device of FIG. 1;

FIG. 4 is a separate plan view of the gravity weight and tether elements of the device of FIG. 1;

DETAILED DESCRIPTION

Figure 5:
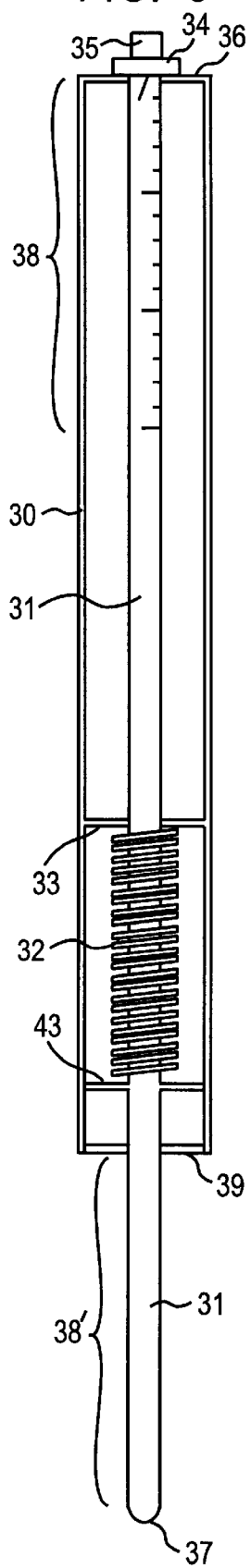
FIG. 5 is a partially cut-away side view of an upright spring loaded sand gauge of the present invention.

A first embodiment of the advantageous sand gauge of the present invention is illustrated in FIG. 1 and comprises a gravity drop spike sand gauge. The partially cut-away side view of the upright device illustrated in FIG. 1 shows all of the parts of the device. As illustrated in FIG. 1 the various parts of the device are built on or into an elongate tube 11 which is separately illustrated in FIG. 2. Tube 11 may be a clear material, such as a clear plastic, polycarbonate being a preferred material for such tube.

Spaced from the lower end of tube 11 is a region 12 of the length of the tube which is marked with graduated markings indicative of how far into bunker sand being tested a gravity drop spike penetrates. This region 12 may be accompanied by a groove or slot 13 through the thickness of the tube and extending parallel to the axis of the tube a desirable distance, such as a distance corresponding to the length of graduation markings 12. The length or distance over which the graduation markings appear may, for example, be ten centimeters (10 cm). As discussed later herein, an indicator marker, finger or needle may be connected to a gravity drop spike located within the tube so that the indicator marker, needle or finger will travel along the length of the groove 13 pointing to a location along the graduated markings 12 indicating the amount of sand penetration by a gravity drop driven spike which has been driven downwardly within the bottom portion of tube 11.

The lowermost end of tube 11 may have a stabilizer plate 14 attached thereto, and the upper end of the tube is prepared to receive and connect to a pulley or other capstan-like surface over which a tether strand may pass and be guided. As shown at the top of FIG. 1, pulley or capstan-like device 15 is offset so that its circumferential surface is approximately tangent the axis of tube 11.

The sand spike for penetrating bunker sand comprises rod or tube 16, which may have a hard tip insert 17 attached to or in the lower end thereof. For example, spike 16 may comprise an aluminum tube having a steel spike tip insert 17, as separately illustrated in FIG. 3, attached to or within the lower end thereof. The upper end of spike 16 is attached to an index bushing 18 which may comprise a spool-shaped body, preferably made of a relatively low friction material such as nylon. The index bushing is generally cylindrical, preferably having the end portions thereof of a diameter just less than the inside diameter of tube 11, with the central portion of the index bushing having a somewhat lesser diameter. One end of index bushing 18 may have a hole bored axially therein to receive the upper end of tube or rod 16.

When index bushing 18 is placed within the lower portion of tube 11 with rod or tube 16 mounted therein, the rod or tube 16 is located substantially coaxially with tube 11. The lower end of spike rod or tube 16 is maintained in this substantially coaxial alignment by a spacer 19 which also may be made of a relatively low friction material such as nylon, and fitted within the bottom of tube 11 with a central hole or bore therein having a diameter just in excess of the outside diameter of spike tube or rod 16. A marker, needle or finger 23 on the upper portion of rod or tube 16 or the lower portion of index bushing 18 indicates, in conjunction with graduated markings 12, the amount of downward displacement of spike 16.

In the upper end of tube 11 there is also mounted a cylindrical gravity drop weight member 20, one kilogram for example, the upper end of which is attached to one end of a tether 21 which passes over pulley or capstan-like device 15. Tether 21 is longer than the open internal length of tube 11, and the other end of tether 21 hangs loosely on the outside of tube 11, and may include at its opposite end a minimal counter weight 22 for maintaining the tether relatively straight and preventing the external end of the tether from slipping into the top of tube 11. Gravity drop weight 20, tether 21 and minimal counter weight 22 are illustrated in FIG. 4, separately from the remainder of the device.

In use, the tether is pulled outwardly so that gravity drop weight 20 rises to a specific location near the top of tube 11. The entire device is oriented vertically with its lower end, stabilizer plate 14 and tip 17 of spike 16 flat on the surface of the bunker sand to be tested, with indicator 23 at the top or zero point of graduation markings 12. Tether 21 is then released permitting gravity drop weight 20 gravitationally to accelerate downwardly impacting the top of index pushing 18 and driving spike 16 and its tip 17 downwardly into the bunker sand being tested a distance indicated by a new location of marker 23' at some point below the initial or zero point of graduation markings 12.

In this specification the term "sand" means "sand or like granular material" replacing turf or soil in a bunker. By conducting such tests in a number of different sands or sand conditions, data corresponding to sand characteristics and the playability of sand shots from sand bunkers including such sand conditions can be developed so that individual players can, during practice sessions, correlate their club selection and swing choices to correspond to known successful shotmaking from sand yielding the penetration measurements.

Figure 6:
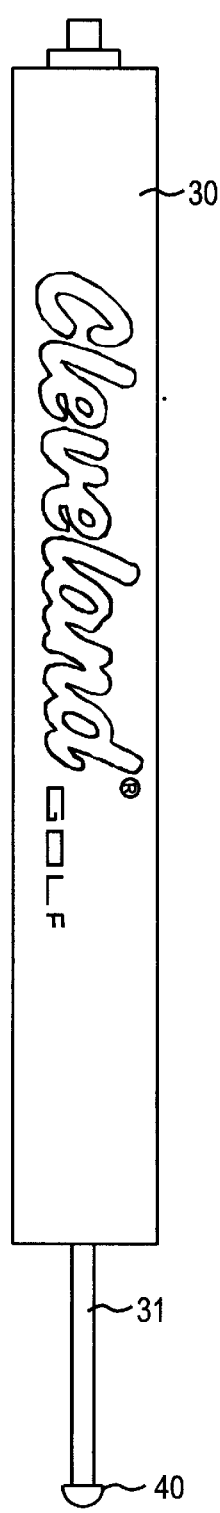
FIG. 6 is a side view of the exterior of a spring loaded sand gauge like that of FIG. 5, when in at-rest position.
Figure 7:
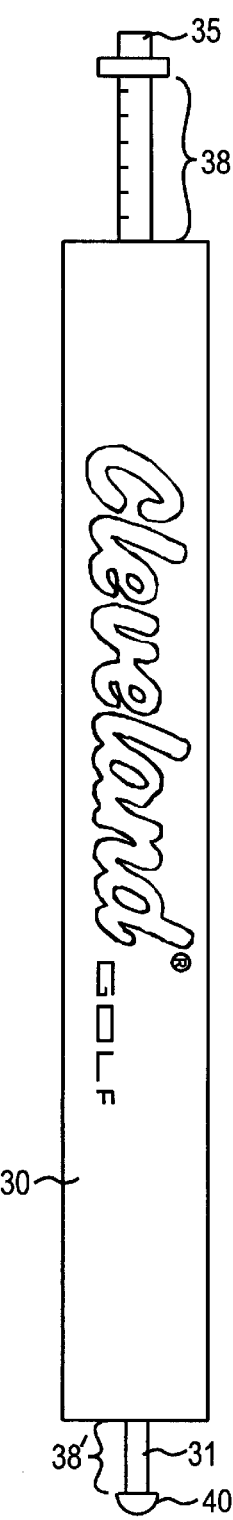
FIG. 7 is a side view of the exterior of a spring loaded sand gauge like that of FIG. 5, when in an actively loaded measuring condition.

Another and preferred embodiment of the advantageous sand gauge of the present inventions is illustrated in FIGS. 5–7. This preferred embodiment is called a spring loaded sand gauge because an active element of this device is a spring which provides a constant load against which the hardness, bulk density or penetrable depth of sand is measured, regardless of the particular location in any sand trap, or different sand traps, where the device is used to measure characteristics of bunker sand.

As illustrated in partially cut-away view in FIG. 5, the spring loaded sand gauge comprises an exterior frame 30 which is illustrated as a cylindrical tube, although other open frame structures or closed or semi-closed parallelopipeds may be used with similar results. Mounted within cylindrical frame 30 is probe/gauge shaft 31 which is mounted approximately coaxially within cylindrical frame 30 and adapted to slide in the axial direction of both shaft 31 and cylindrical frame 30. Within frame 30 and surrounding or otherwise adjacent shaft 31 is spring 32, here illustrated as a coil spring surrounding shaft 31. The upper end of spring 32 abuts a stopper member 33 affixed within frame 30. The lower end of spring 32 abuts a pin or other abutment device attached to shaft 30 and extending radially therefrom a sufficient distance to support and prevent downward movement of spring 32 vis-a-vis shaft 31. In FIG. 5 this lower abutment which stops the lower end of spring 32 vis-a-vis shaft 31 is illustrated as an annular plate 43 against which the lowest portion of spring 32 presses as shaft 31 rises in frame 30.

The top end of shaft 31 bears a stopper or nut 34 for preventing end 35 of shaft 31, which protrudes through top 36 of cylindrical frame 30, from traveling downwardly toward the interior of frame 30. Immediately below top stopper 34 the length of shaft 31 bears graduated markings for reading the amount of penetration achieved by the lower tip end 37 of shaft 31 when lower top 31 is plunged into bunker sand being tested. The total length 38 of the graduated markings on the upper end of shaft 31 corresponds to the total extended length 38' by which shaft 31 protrudes downwardly from the lower edge of cylindrical frame 30. The length 38 of graduated markings is preferably ten centimeters (10 cm). Lower end 39 of cylindrical frame 30 is also preferredly fitted with a base cap having a central opening through which the lower portion of shaft 31 protrudes.

In practice, the frame or cylindrical housing 30 may comprise tubular material such as ABS tubing or other suitable plastic or metal material. The end caps 36, 39 and spring stops 33 and 43 may comprise aluminum or plastic disks, and probe/gauge shaft 31 may be an aluminum or reinforced plastic rod, of suitable diameter, such as about ⅝ inch, for example. Spring 32 may be a spring steel or stainless steel spring having an inside diameter of ⅝ an inch, for example, and outside diameter of about 1¾ an inch, for example, with compressed length of about 7 inches and load of about 25 Kg per square inch, for example.

As shown in FIGS. 6 and 7, lower tip 37 of probe/gauge shaft 31 may comprise a specially contoured tip 40 whose diameter, and thus horizontal surface area, are designed to correlate with the spring used in the device. The cross-sectional area of the exposed lower end or tip 37, 40 of the probe shaft and the force of the spring or biasing device 32 are selected so that the displacement of the shaft, when the device is used in golf course sand bunker sand, will be indicated along the length 38 of the graduation markings.

FIG. 6 shows an exterior view of the spring loaded sand gauge like that of FIG. 5 wherein the probe/gauge shaft 31 is in its at-rest position fully extended out the bottom of the device. Conversely, the view of FIG. 7, which is a similar view to that of FIG. 6, shows the probe/gauge shaft 31 in an actively loaded measuring condition wherein the lower extension 38' of probe/gauge 31 has been displaced upwardly substantially into the interior of tubular frame 30, while upper end 35 of probe/gauge shaft 31 is likewise displaced substantially upwardly revealing a certain portion of the graduated measurement markings 38, the specific length of such markings corresponding to the amount of upward displacement of the lower tip 40 of probe/gauge shaft 31.

In use a user simply places the lower tip 37, 40 of the spring loaded sand gauge on the surface of bunker sand to be tested, while gripping the exterior of cylindrical frame 30, and then pushes cylindrical frame 30 vertically downward whereby the tip 40 of probe/gauge shaft 31 penetrates a certain distance into the bunker sand being tested and the resistance of the sand and resistance of spring 32 result in an equilibrium situation wherein the bottom 39 of frame 30 is just touching the surface of the sand, and probe/gauge shaft 31 is no longer being displaced upwardly within cylindrical frame 30. In that condition, the length of graduated measurement markings 38 exposed above top plate 36 of the gauge can be recorded as a measure of the hardness, bulk density, or comparative hardness or comparative bulk density, of the sand in the particular location at which that test result was observed.

Probe/gauge shaft 31 has a single diameter length-wise profile, as shown in FIG. 5. Tip 40, as shown in FIGS. 5 and 6, preferably has a substantially hemispherical tip having a diameter equal to or greater than the maximum diameter of probe/gauge shaft 31.

As with the first embodiment, by conducting such tests in a number of different sands or sand conditions, data corresponding to the sand hardness or bulk density characteristic, and the corresponding playability of sand shots from such sand, can be developed so that individual players can, during practice sessions, correlate club selection and swing choices to correspond to sand penetration measurements and the effects of corresponding sand conditions upon club and swing choices in known circumstances.

The following tabular list generally describes characteristics of bunker sand tested with the devices of the present invention, corresponding to approximate probe/gauge penetration readings observed in such tests:

| Probe/Gauge Penetration: | Sand Characteristics: |
| --- | --- |
| less than 2 cm. | Quite to very hard, compact sand. |
| 2 to 4 cm. | Firm sand; or wet sand; may slightly cover shoe soles; golf balls not likely to bury in it. |
| 4 to 7 cm. | Dry, soft sand. |
| greater than 7 cm. | Very soft sand; shoes sink easily; high potential for substantially buried golf ball lies. |

Not only will such sand gauges provide players some knowledge of sand conditions during practice sessions to correlate with club selection and swing choices, but such sand gauges will enable greenskeepers or golf course superintendents to prepare the sand conditions in various traps around a golf course with some knowledge of whether or not those conditions are similar or greatly divergent. For example, many course superintendents may seek to have sand conditions which are quite similar in all sand traps throughout a golf course. While other course superintendents may seek to have the conditions in fairway bunkers be much harder or more dense than sand conditions in greenside bunkers.

Still further, the use of the advantageous sand gauges of the present invention may provide the opportunity for sand conditions in various courses to be compared, graded, or even regulated for certain tournament purposes or for handicap or "slope" determination purposes.

Even further, the fitting of sand wedges or other clubs often used for sand shots may vary depending upon sand conditions as well as other aspects of clubhead design and player swing characteristics. A club fitter having some knowledge of relative characteristics of sand, determined by a standard testing technique, in which test swings are made as a basis for fitting an appropriate sand iron to a particular player, will facilitate a fitting which is more likely to be advantageous for that player.

While the advantageous sand gauges of the present invention have been illustrated in specific preferred embodiments herein, those skilled in the art will understand that various modifications of the advantageous gauges of the present invention may be made without departing from the scope and spirit of the invention as stated in the following claims.

What is claimed is:

1. A sand penetrability gauge for testing golf course sand bunker sand, comprising:

a probe shaft for penetrating into golf course sand bunker sand, said shaft having a blunt tip having a maximum thickness greater than or equal to a maximum thickness of said shaft;

means for reproducibly applying a predetermined force to advance the probe shaft into golf course sand bunker sand, said means for applying a force comprising an elongate support frame having the probe shaft slidably mounted therein and biasing means located between the frame and probe shaft for reproducibly applying the force of said biasing means to said probe shaft, said means for applying a force selected for use with golf course sand bunker sand, means associated with said probe shaft and force applying means, for measuring displacement of the probe shaft vis-a-vis the force applying means, and a probe stop attached to said probe shaft at a position external to said elongate support frame, for limiting travel of said probe shaft in said elongate support frame.

2. The sand gauge of claim 1, wherein a cross-sectional area of the probe shaft and the predetermined force of the force applying means are selected so that the measuring means will provide a displacement measurement when the sand penetrability gauge is used in golf course sand bunker sand.

3. The sand gauge of claim 1, wherein said support frame is an elongate tube, the probe is slidably mounted substantially coaxially within said tube, and the biasing means comprises a coil spring substantially coaxially surrounding the probe shaft, an upper spring stop connected to the inside of said tube with the top of said coil spring abutting said upper spring stop, and a lower spring stop connected to the probe shaft with the bottom of said coil spring abutting said lower spring stop.

4. The sand gauge of claim 3, additionally comprising measuring indicia located on one of the tube and probe shaft, and an indicator located on the other of the tube and probe shaft, so that the indicator indicates vis-a-vis the measuring indicia displacement of the shaft vis-a-vis the tube.

5. The sand gauge of claim 4 wherein when said probe shaft is not displaced vis-a-vis the tube, the lower end of the probe shaft extends outside the bottom of the tube a distance corresponding to the axial extent of said measuring indicia.

* * * * *